United States Patent [19]

Pfeiffer

[11] Patent Number: 4,613,568

[45] Date of Patent: Sep. 23, 1986

[54] METHOD FOR RELEASE AND SEPARATION OF PARASITES OR PARASITE EGGS FROM MEAT

[75] Inventor: Gottfried Pfeiffer, Eching, Fed. Rep. of Germany

[73] Assignee: A/S N. Foss Electric, Denmark

[21] Appl. No.: 603,688

[22] Filed: Apr. 25, 1984

[30] Foreign Application Priority Data

Apr. 25, 1983 [DE] Fed. Rep. of Germany ....... 3314937

[51] Int. Cl.[4] .......................... C12Q 1/38; A23L 1/31; C07G 17/00; C07G 15/00
[52] U.S. Cl. ...................................... 435/23; 210/335; 210/383; 210/398; 426/56; 426/478; 426/479; 426/480; 435/261; 435/267; 435/268; 435/287; 435/814
[58] Field of Search ..................... 426/55, 56, 59, 231, 426/479, 480, 478; 435/23, 261, 267, 268, 814, 287, 317; 210/335, 383, 390, 398

[56] References Cited

U.S. PATENT DOCUMENTS 4,402,873  9/1983  Vollmer et al. .................. 426/56 X

FOREIGN PATENT DOCUMENTS

| 0059403 | 9/1982 | European Pat. Off. . |
| 908968 | 4/1954 | Fed. Rep. of Germany . |
| 1205041 | 11/1965 | Fed. Rep. of Germany . |
| 2063502 | 6/1971 | France . |
| 7458 | 1/1977 | Japan ................................. 426/59 |

OTHER PUBLICATIONS

The Effect of Sub-Micron Filtration on the Biological and Shelf-Life Stability of Beer, Millipore Filter Corporation, Bedford, Mass. 1962, pp. 1–17.

*Primary Examiner*—David M. Naff
*Attorney, Agent, or Firm*—Webb, Burden, Robinson & Webb

[57] ABSTRACT

A method and device is disclosed for the release and separation of substances such as parasites or parasite eggs from meat. In the method, meat is agitated with pepsin and filtered through a series of at least two filters, the last of which retains the parasites or parasite eggs. The device includes a reactor which tapers downwardly, and which has in its lower part an outlet valve connected via a conically widening part with a separator device. The separator device includes a cylindrical connecting piece which accepts holder rings for holding one or more filters or sieves in releasable connection.

10 Claims, 3 Drawing Figures

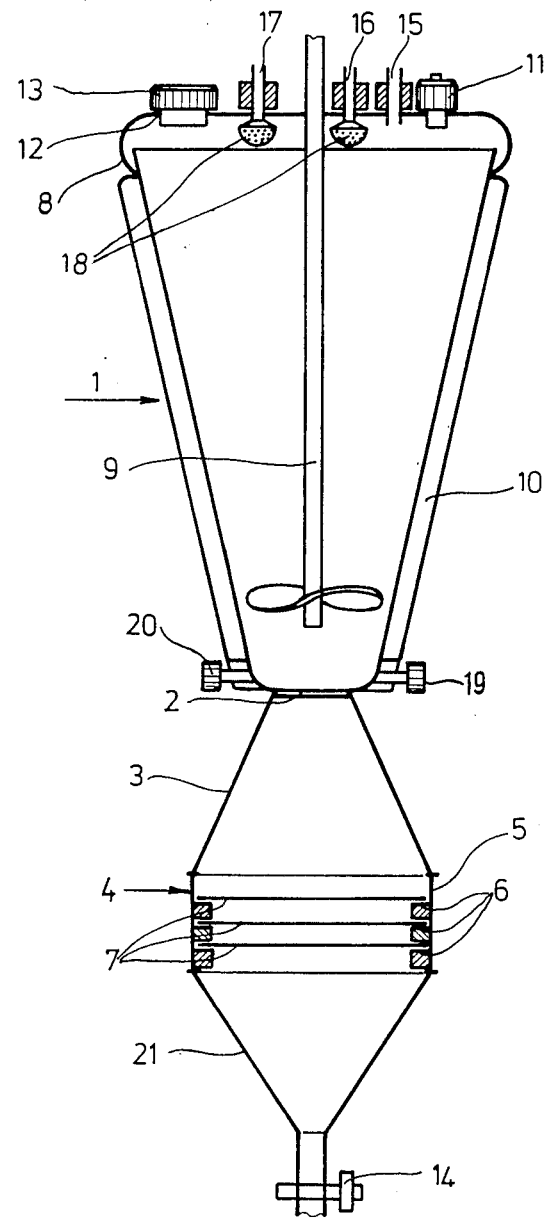

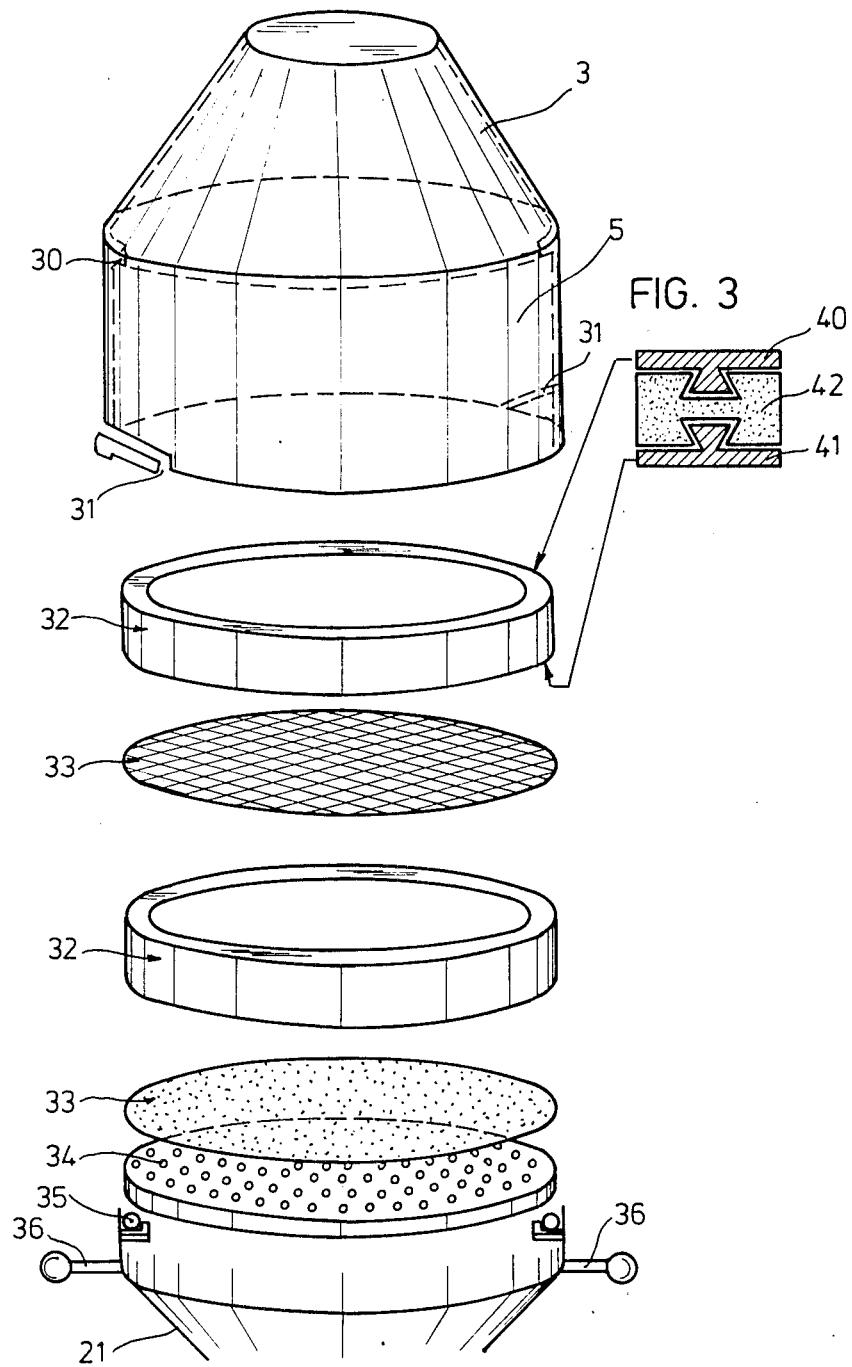

METHOD FOR RELEASE AND SEPARATION OF PARASITES OR PARASITE EGGS FROM MEAT

The invention relates to a device and to a method for production or release and separation of substances or particulate products of fluid, plastic or solid material and to use of the device.

In the fields of analytical investigation and the extraction of substances or particulate products by their production and/or their isolation from a fluid or plastic or solid material, for example a biological material, there exists a need for a device and for a method with the aid of which the production or release of substances and their separation can be carried out as quickly as possible. In particular, such devices are of interest which allow automization of the individual steps carried out therein. To the extent that it is possible to carry out the steps for the production or release of a substance or of a particulate product and its separation from the remaining mixture in an individual device and thereby to automize the method parameters in the individual partial steps, as well as the addition of mixing additive, Beund gassing and degassing, and also the rinsing or washing process lying between the individual investigations or experiments, such methods may be carried out in series. In this manner, it is possible to save considerable personnel costs and to optimize the associated method in respect of its purpose of use.

The object of the present invention is to make available a device and a method for the production or release and separation of substances or particulate products from fluid, plastic or solid material.

This object is achieved according to the invention by a device of the type described in the preceding which comprises a reactor vessel tapering downwardly which has an outlet valve in its lower part and is connected via a conically widening part to a sequentially connected separator means, the separator means including a cylindrical connecting member adapted to receive holder rings for the support of at least one filter or sieve, and including releasable opening means for removal of at least one said filter or sieve.

Furthermore, a method of the above-described type is made available in which with use of the device according to the invention the released plastic or solid material together with one or more liquids is treated in a reactor chemically and/or physically, the mixture contained being directed via the outlet valve located in the lower part of the reactor to a separator device in which with the aid of one or more filters a separation of the same into a fluid and one or more solid phases is performed, which phases may differ from one another by the size of their corpuscular component parts. The arrangement of the filter system of the separator device can for this reason also be so constructed that components above a certain corpuscular size or molecular size are retained in the liquid phase and this forms the basis for further investigation or treatment.

The invention includes in particular a method with use of the device according to the invention for the analysis of pork for the presence of trichina.

The use of the device according to the invention may be applied in numerous fields of an analysis and in the extraction and isolation of substances or particulate products and especially in the technological studies using the smallest amounts of raw material and process compositions.

The device according to the invention is in this field also of particular interest in so far as it provides a method which enables in true and coloidal solutions and in dispersions and emulsions, by precipitation, coagulation and agglomeration or by coalescence, specific aggregates to be produced, separated and if necessary microscopically investigated. In these cases, it often happens that it is important during or after the production of the aggregates to decolorize the solutions, dispersions and emulsions chemically or for example by means of an absorption means such as animal carbon. Just as often it is however important during or after the production of the aggregates to mark the solutions, dispersions, or emulsions with dyes or radioactive substances or to apply other substances. In serological studies in numerous investigations, an agglomeration and separation of antigen-antibody associates and/or the extraction of a liquid phase released by such associates occurs.

FIG. 1 shows a representation of the device according to the invention. The reactor 1 which preferably tapers downwardly in a funnel form or conically serves for the reception of the plastic or solid material. By means of a removable lid part 8, the reactor 1 can be closed in a liquid-tight or gas-tight manner. A valve 11 located in the lid part 8 serves for pressure equalization or the addition of for example pressurized air. The lid part 8 includes moreover an opening 12 for the supply of the reactor with test substance. This opening is preferably closed in a vacuum and pressure-tight manner by means of a stopper 13 having a bayonet connection. Moreover, centrally of the shaft a comminuting device 9 extends into the lid part and is preferably represented by a rotating knife which preferably can be connected for continuously variable rotations up to $3 \times 10^4$/min. or is actuated by manual switching.

The entry valves 15, 16 and 17 are preferably closable in a pressure-tight manner and can be provided with spray nozzles 18.

The central part of the reactor 1 is surrounded in a fluid-tight or gas-tight manner by a sleeve 10 by means of which heat can be supplied or removed through the reactor wall via a circulating liquid or a suitable gas. A temperature in the range of from $-60°$ C. to $250°$ C. is preferred, particularly in the range of from $-10°$ C. to $60°$ C. Beneath the sleeve a screw opening 19 or 20 is located through which access may be made with a temperature sensor or an ion-sensitive electrode or a conductivity meter or a viscosity meter or another measuring instrument.

The reactor 1 tapering downwardly possesses in its floor part an outlet valve 2 which represents a connection of the reactor 1 to the subsequent separator device 4. The outlet valve 2 can for example be a magnetic valve, a two-part cock or another suitable valve.

The lower part of the reactor 1 with the outlet valve 2 continues from a conically widening part 3 and is releasably connected to this by a bayonet or screw connection, which part 3 is connected to the subsequent separator device 4.

The separator device 4 consists of a cylindrical connecting piece 5. This connecting piece 5 carries holders 6 which serve for holding one or more filters or sieves 7. The connecting piece 5 is located in fixed connection either with part 3 or part 21 and is in corresponding releasable contact, for example via a screw or bayonet connection, with part 21 or part 3; or the separator device 4 is in releasable contact both with part 3 and part 21.

Separator device 4 is provided on its lower end with an outlet valve 14.

FIG. 2 represents a preferred construction for the separator device 4. The connecting piece 5 is located in fixed contact with part 3. 30 represents a press surface for an upper rubber seal. 31 is a catch for a bayonet connection. The connecting piece 5 accepts distance holder rings 32, possible with an inserted seal. Filters 33 are located in each case between the distance holder rings 32. A membrane carrier-sieve disc 34 serves as support for the filter with the finest perforations and is mounted on an O-ring 35. Catch member 36 serves for locking by means of a bayonet connection. The connecting piece 5 is thus in releasable contact with part 21.

FIG. 3 is a cross-sectional representation of a preferred distance holder ring, consisting of the profiled rings 41 and the intermediate lying rubber seal 42.

With the aid of the device according to the invention a method for the production or release and separation of substances or particulate products from liquid or plastic or solid material can be carried out. For the purpose, one introduces into the reactor 1 either only fluid or the plastic or solid material together with a liquid and carries out a chemical and/or physical treatment.

The introduced substance can be a solvent for one or more of the substances to be released, such as for example water, buffer solution or an organic solvent.

The chemical treatment can for example be a treatment with a possibly strong acid or base, a coloring or decoloring substance or solution, or a gas or can be an enzymatic investigative method with the aid of a buffered enzyme solution or a serological reaction. In the case of the enzymatic treatment of the said material, the liquid introduced into the reactor is preferably water or a buffer solution. As an enzyme for the enzymatic treatment, hydrolases are particularly suitable, in particular proteolytic enzyme but however also oxidases, reductases, transaminases and a plurality of other enzymes.

In each case according to the type of chemical treatment, the mixture located in the reactor can be brought to the appropriate temperature and be thermostatically maintained at the same.

The physical treatment of the said material takes place particularly advantageously by means of heat or cooling treatment, for example for the production of coagulation, crystallization or of melting processes or comminution of the same. For the comminution one uses a suitable comminuting device such as for example preferably a rotating knife. It is also suitable however to use a stator possibly profiled on its upper surface within which a rotor driven by a motor lying preferably outside the stator is rotated with a correspondingly profiled upper surface. The comminuting device is preferably driven continuously up to $3 \times 10^4$ rpm. According to further embodiments, the drive of the comminuting device takes place by manual individual switching or automatically according to a preselected time switching program.

According to a further modification, a physical treatment with if necessary comminution or agglomeration of the said material by means of ultrasonics can be employed. In this case, the ultrasonic wave is preferably introduced via a shaft 9 introduced through the lid part 8 or the wall of the reactor.

To the extent that no comminuting device is necessary for the treatment of the said material, also a stirring device can be introduced through the lid part 8 or through the wall of the reactor.

It is particularly advantageous to combine a physical treatment with a chemical treatment thus for example first to carry out a physical comminution of the plastic or solid material which subsequently, for example by enzymatic treatment, proceeds further.

The filter or filters are so sealed that in the passage of the fluid part of the batch through the filter or filters there is only one path for the liquid to escape, that is to say through the sieve or porous openings of the filter or filters.

The mixture contained for the chemical and/or physical treatment is transferred via the outlet valve 2 into the separator device 4 in which with the aid of one or more filters is separated into a fluid and one or more solid phases.

The fluid phase produced in the separation can in this connection be a solution, dispersion or an emulsion.

The separation in the separator device, which takes place by means of one or more filters, sieves or sieve membranes, can take place with pressure application by the valve 11 or by application or a vacuum in the lower part of the separator device.

The separation in the separator device is preferably carried out by means of one, two or three filters, sieves or sieve membranes, in which connection with the use of two or more filters etc. particles of differing size can be held back on the same. The porosity of the individual filters reduces in this connection in the flow direction.

In this manner, one obtains on the filters separated solid phases from corpuscular component parts which differ from one another in respect of the individual volume and perhaps the total volume of the corpuscular component parts in the dependence upon the cross-section of the pores or sieve openings.

The separation in the separator device takes place according to a modification according to the invention by means of two or three different filters. The filter or sieve lying adjacent the outlet valve consists preferably of a synthetic or metal mesh welded to the flat upper surface and having sieve openings which in particular are lozenge-shaped and have a longitudinal diameter of 1 to 2 mm and a cross diameter of 0.7 to 1.4 mm.

The second sieve following in the flow direction is preferably a sieve with a flat upper surface and sieve openings with a diameter of 0.18 to 0.6 mm, preferably 0.4 mm.

The third sieve is a transparent membrane sieve carried by a sieve disc having sieve openings of diameter 0.3 to 1 mm, preferably consists of polycarbonate, and has sieve openings of diameter from 8 to 30 $\mu$m, preferably 12 $\mu$m.

From the preceding said three filters or sieves, according to one embodiment according to the invention the second can be omitted so that only a combination of two of the preceding said filters is used.

According to the invention it is preferred for the separation of the comminuted mixture to use a set of plurality of transparent membrane sieves having sieve openings of diameter up to 180 $\mu$m whose pore size reduces in the flow direction.

A particular advantage of the method according to the invention with use of the device according to the invention consists in that with small expenditure either manually or automatically a subsequent rinsing process can be carried out. Moreover, it is possible in each analysis method to clean the device according to the invention easily by manual or automatic means.

The method according to the invention can be used for the production or release and separation of substances or corpuscular products in any fields. Since according to the invention a combination of the method steps provides production or release and separation, in this manner it is particularly easy to determine analytically substances or particles which can be produced and/or released or disaggregated and separated from a complex material to be analysed or investigated. Moreover, the method according to the invention is suitable for the isolation of substances or particles from complex material.

Thus, the method according to the invention is for example particularly applicable for the release and separation of for example parasites or parasite eggs or nondigested particles in stool samples or drains, starch corns from raw potato, etc., spices from food, oxalate cystals from bark, pollen from pollen conglomerates, bacteria, and viruses from sausage meat, cell organelles, such as for example nuclei, mitochondria, etc. from biological material. Moreover, also enzymes, metabolites, or diverse macromolecules isolated or enriched according to the principle of ultrafiltration can be concentrated or separated with the aid of the method according to the invention. For each of the examplary cases of use, filters and filter membranes of various porosity are commercially available and can be specifically combined according to the purpose of use in the separator device.

Finally, the method according to the invention is suitable also for the preparation of soil samples and release and separation of the substances to be investigated. With the preceding mentioned methods of analytical investigation of substances or particulate products of biological material, the analysis of trichina in pork is of particular interest.

For more detailed explanation of the method according to the invention with use of the device according to the invention, there will now be described an improved method for the analysis of trichina in pork. The invention is however not limited to this embodiment.

METHOD FOR THE ANALYSIS OF TRICHINA IN PORK

I. Device

This consists of the apparatus according to the invention consisting of a reactor part with connected separator device with a combination of preferably four sieve discs of diameter of 47 to 50 mm. The preferred constitution of the sieve is described under "III. Preferred Method for the Analysis of Trichina in Pork with the Apparatus According to the Invention".

The outlet of this apparatus extends in a vacuum-type manner into a vacuum container evacuated by means of a water stream pump nd comparable in its function to a laboratory suction flask, the vacuum container having an outlet cock on its floor for removal of liquid phase. By opening of the outlet valve 2 and the outlet cock of the separator device 4 the batch is brought into the reactor under vacuum so that its liquid part passes the separator device when the valve 11 is open or the lid opening 12 is open. The intermediate space between reactor wall and sleeve 10 is connected to the circulation pump of a water bath via a sleeve for the supply and a sleeve for the removal of water thermostatically controlled at 46° C. Above the apparatus are mounted three device containers each of whose outlets is connected in each case via a dosing pump and by means of tubes to the inlet valves 15, 16 and 17 mounted on the lid 8 and in each case sealably closable. The inlet valve 16 provided for the introduction of 0.75% HCl solution and mounted adjacent the shaft of the rotating knife and the inlet valve 17 open in each case into a spray nozzle by means of which coarse particles sticking to the reactor wall can be sprayed off.

Concerning the said device containers, there is provided a 2 to 5 liter device container for 5% pepsin solution provided with HCl at pH 5.5, a 10 liter device container for 0.75% HCl and a 10 liter device container for water of pH 1.1.

Moreover, a glass plate of size $70 \times 80 \times 3$ mm and a glass plate of $60 \times 60 \times 3$ mm, the latter having parallel lines scored as a spacing of 3 mm, and a microscope with 20 and 40 times magnification and a stopped down condenser are provided.

II. Materials (a) Test Material

One or more walnut-size muscle pieces from the diaphragm column of butchered pork or other trichina-suspected examination material.

(b) Reagents (1) Pepsin, 30,000 E/g
(2) Concentrated hydrocholoric acid
(3) Octanol (c) Solutions (1) 5% aqueous pepsin solution
(2) 0.75% and 0.5% HCl solution
(3) Water adjusted to pH 1.1

III. Preferred Method for the Analysis of Trichina in Pork with the Apparatus According to the Invention The methods described in the following have three decisive advantages compared with the state of analytical chemotechnology:

1. the very rapid mechanical and chemical comminution,
2. the very rapid separation of trichina from the batch,
3. the very rapid simple and reliable detection of trichina on the transparent membrane sieve.

First Preferred Method (a) In each case 1 g of diaphragm muscle from twentyfive to forty-five pigs are combined to one sample and introduced through the opening 12 in the lid of the reactor which subsequently or before is supplied with 100 ml of part 5% aqueous pepsin solution of pH 5.5 related to the weight of the combined sample and whose wall is brought to a temperature of 46° C. by circulation of liquid between it and its sleeve. Then the opening 12 is closed.

(b) The combined sample is now comminuted with a blunt rotational knife 9 until the non-binding membrane containing part of the skeletal musculatur is predominantly dissolved or appears coarsely dispersed. This comminuting process takes altogether one to three minutes with a knife rotational speed of 7000 to 12,000 rpm. During the mechanical pre-comminution coarse components of the combined sample are from the beginning onwards rinsed off the reactor wall or the lid 8. The rinsing off is carried out by the introduction of 0.75%

HCl solution under pressure through an inlet 16 entering through the lid into a spray nozzle 18.

(c) In the remaining process the rotational speed of the knife is reduced to from 50% to 5%, preferably 10% of the initial rotational speed and 0.75% HCl added until the batch has a pH of preferably 1.1, but in any case 0.8 to 2.2. This is achieved volumetrically in that altogether 400 ml of 0.75% HCl solution are added.

(d) Finally, the batch is stirred for preferably eight minutes or until the main part of the trichina is released from its cistation, only a few particles containing connective tissue or blood vessels of about carroway seed size are present and the liquid part of the batch with its dissolved, dispersed or corpuscular component parts of a size smaller than 12 µm can be passed even through the lowest sieve of the separator device, i.e. preferably through a transparent membrane sieve with a pore size of diameter 12 µm. The fine foam arising in the batch during this mechanical and enzymatic comminution is preferably broken up before separation of the trichina. This is achieved in that approximately 0.5 ml of octanol are added to the batch directly before the switching off of the rotational knife from a drop pipette through the lid opening 12.

(e) The separation of the trichina and the connective tissue and/or blood vessel fragments mentioned under (d) is preferably achieved by means of a vacuum in that the valves 11, 2 and 14 are opened and the liquid part of the batch passes in the flow direction the sequence of four filter sieves which have the following features:

No. (1) is a synthetic or metal web preferably welded to a flat upper surface with preferably lozenge-shaped sieve openings with a longitudinal diameter of 1 to 2 mm and preferably 1.5 mm and a cross-section of 0.7 to 1.4 mm, preferably 1 mm.

No. (2) is a synthetic or metal web preferably welded to a flat upper surface having sieve openings with a diameter of 0.3 to 1.2 mm, preferably 0.9 mm.

No. (3) is preferably a sieve with a flat upper surface and sieve openings having a diameter of 0.18 to 0.6 mm, preferably 0.4 mm.

No. (4) is a transparent membrane sieve carried by a sieve hole plate preferably having sieve openings of diameter 0.3 to 1.0 mm, which membrane sieve preferably consists of polycarbonate and has sieve openings of diameter 8 to 30 µm, preferably 12 µm.

The separation of the trichina takes place by means of vacuum or in addition to vacuum with the additional aid of pressurized air which is introduced through the valve 11 with the inlet valves 15, 16 and 17 closed and the lid opening 12 closed.

(f) After complete passage of the liquid part of the batch through the filter, the valves 11, 2 and 14 of the series are closed and the reactor is rinsed with 150 ml of water through the spray nozzle 17 brought to a pH of 1.1 with HCl. Thereafter, the rinsing water is removed through openings of the said valves, 11, 2 and 14 by means of vacuum through the separator device so that a rinsing of the separator device is achieved also.

(g) To examine the trichina, the polycarbonate membrane is removed after decoupling of the separator device the sediment side being held downwardly if possible in the absence of air bubbles laid on a glass plate supplied with two or three drops of water and after the addition of two or three drops of water as far as possible in the absence of air bubbles is covered with a second glass plate and examined microscopically for indications of trichina.

The separator device is subsequently provided with the sieves of the said properties and sequence, which sieves after their use in an earlier method process have been cleaned for two to twenty-four hours or even longer in a 5% pepsin solution of pH 1.2, and thereafter rinsed with strong water jets and possibly dried before placing in store.

A method which deviates partially from this method consists in that the mechanical and chemical comminution according to (a) to (d) takes place after the application of a vacuum (not too high) in the reactor and its hermetic sealing against the atmosphere. This provision has the advantage that no or very little foam arises and thereby the addition of octanol can be omitted. For the breaking of foam sufficiently and also on technical grounds it is of advantage also to use a method in which the batch is comminuted under atmospheric pressure but before breaking of the foam directly before separation in the reactor a momentary vacuum is applied and after its direct removal is immediately separated.

Second Preferred Method

A very strongly simplified method for the investigation of trichina with apparatus according to the invention consists in the following:

The apparatus preheated to 46° C. is supplied through the lid opening 12 with 30 g of sample material and 100 ml of 5% pepsin solution and thereafter comminuted for three minutes with a rotational knife speed of 12,000 rpm. After switching off of the motor a 0.75% hydrochloric acid solution is added through the lid opening 12 with a measuring beaker of 400 ml and the lid opening is closed. Thereafter, the batch is again stirred for one minute with a rotational knife speed of 12,000 rpm and in the following seven minutes with a rotational speed of 1000 to 2000 rpm. Thereafter, the lid opening 12 is opened, 12 ml of octonal added, the motor immediately switched off and as soon as the rotational knife is stationary the outlet valves 2 and 14 are opened and the fluid part of the batch is separated by means of vacuum.

After the separation, the valves 14, 2 are closed after the addition of 150 ml of HCl solution of pH 1.1 also through the lid opening 12, the rotational knife is brought for about one second to 12,000 rpm, then immediately switched off and the rinsing water removed by means of vacuum through the sieves.

Instead of using a vacuum, or in addition to a vacuum also in this simplified method the separation can be carried out with the additional aid of pressurized air.

Third Preferred Method with a Miniaturized and Simplified Apparatus for the Use in Individual Slaughtering or Small Numbers of Slaughters Outside the Laboratory Miniaturization of the apparatus is achieved in that the reactor beaker has a volume of only about 250 ml and the simplification is achieved in that the sleeving of the reactor serving for thermostatic control is not provided; secondly in that the reactor lid sealable in an air-tight manner by means of a bayonet connection to the reactor beaker is provided only with a valve 11 for introduction of air by means of a rubber ball for the purpose of achieving a pressure of at least one bar and the valve 11 is a check valve; thirdly preferably in that the motor rotates the blunted rotational knife with a non-regulatable constant rotational speed which in the unloaded condition is preferably 6000 to 12,000 rpm and is provided with a variable adjustable automatic interval switch. This interval switch enables alternation of half a minute to five minutes operation and half minute to five minutes rest.

This apparatus is used as follows:

The reactor is provided with a sample of 5 to 10 g preferably 7 g of skeletal musculature and with 1.5 g of pepsin and by means of a measuring beaker with 130 ml of 0.5% HCl solution at room temperature up to 48° C., preferably 48° C.

In the case of an individual slaughtering, the sample consists of an individual approximately walnut size piece of diaphragm column. With two to three pigs an approximately half walnut size or cherry size piece of skeletal muscle is employed. When investigating four to ten pigs the combined sample consists of a number of individual tests of good hazel nut size corresponding to the number of slaughtered pigs.

After the pepsin is stirred with a spatula in the 0.5% HCl, the reactor lid is sealed and the batch comminuted for two minutes. Then the motor is switched on with the interval switch and the batch alternately treated for about one minute drive and about two minutes rest for five minutes altogether. Thereafter, the motor is switched off, a pressure of at least one bar produced in the reactor with the rubber ball and thereafter the outlet valve 2 opened. After passage of the liquid part of the batch through the separator device, the reactor lid is removed, rinsing takes place with 0.5% HCl from the spray flask into the reactor beaker and after rinsing also the reactor inner surfaces is sealed in an air tight manner with the reactor lid. Thereafter, once more a pressure of at least one bar is produced by means of the rubber ball and separation is renewed. The examination of the trichina takes place as described above.

Instead of the 130 ml of 0.5% HCl solution, a buffer solution of pH 1.1 can equally be used.

I claim:

1. A method for the release and separation of parasites or parasite eggs from meat comprising:
   agitating meat with pepsin at about pH 5.5 until the non-binding membrane containing part of said meat is predominantly dispersed;
   adjusting the pH to between 0.8 and 2.2 by the addition of acid;
   continuing agitation until the main part of the parasites or parasite eggs are released and only a few particles containing connective tissue or blood vessels are present; and
   filtering the mixture through a series of at least two filters, the first filter comprising a sieve having openings 1 to 2 millimeters in diameter and the last filter comprising a sieve having pores with a diameter of 12 to 30 microns, whereby the last filter retains the parasites or parasite eggs for microscopic examination.

2. The method according to claim 1 in which agitation is carried out with a blunt knife rotating at 7,000 to 12,000 rpm wherein the pH is about 5.5, and at 700 to 1,200 rpm upon adjustment of the pH to 0.8 to 2.2.

3. The method according to claim 1, wherein a fine foam formed during the reaction is broken up by the addition of a trace of octanol just before filtration.

4. The method according to claim 2, wherein a fine foam formed during the reaction is broken up by the addition of a trace of octanol just before filtration.

5. The method according to claim 1 in which the reaction is carried out under a pressure slightly different from atmospheric pressure to prevent formation of a foam.

6. The method according to claim 2 in which the reaction is carried out under a pressure slightly different from atmospheric pressure to prevent formation of a foam.

7. The method according to claim 1 in which the filter which retains the parasites or parasite eggs is made from polycarbonate.

8. The method according to claim 2 in which the filter which retains the parasites or parasite eggs is made from polycarbonate.

9. The method according to claim 3 in which the filter which retains the parasites or parasite eggs is made from polycarbonate.

10. The method according to claim 4 in which the filter which retains the parasites or parasite eggs is made from polycarbonate.

* * * * *